(12) United States Patent
Gustafsson et al.

(10) Patent No.: US 8,501,435 B2
(45) Date of Patent: Aug. 6, 2013

(54) PROCESS FOR PRESERVING THREE DIMENSIONAL ORIENTATION TO ALLOW REGISTERING HISTOPATHOLOGICAL DIAGNOSES OF TISSUE TO IMAGES OF THAT TISSUE

(75) Inventors: Ulf Peter Gustafsson, Honolulu, HI (US); Jody C. Oyama, Aiea, HI (US); Sara Maria Bergsten, Lund (SE); Andrew Beaumont Whitesell, Kailua, HI (US); Richard W. Lieberman, Ann Arbor, MI (US); Michael Paul Eldred, Kailua, HI (US)

(73) Assignee: STI Medical Systems, LLC, La Jolla, CA (US)

( * ) Notice: Subject to any disclaimer, the term of this patent is extended or adjusted under 35 U.S.C. 154(b) by 763 days.

(21) Appl. No.: 12/587,614

(22) Filed: Oct. 8, 2009

(65) Prior Publication Data
US 2010/0093023 A1    Apr. 15, 2010

Related U.S. Application Data

(60) Provisional application No. 61/195,771, filed on Oct. 9, 2008.

(51) Int. Cl.
*G01N 1/30* (2006.01)

(52) U.S. Cl.
USPC .......................................................... 435/40.52

(58) Field of Classification Search
None
See application file for complete search history.

(56) References Cited

U.S. PATENT DOCUMENTS

| | | | |
|---|---|---|---|
| 6,225,107 B1 * | 5/2001 | Nagle | 435/283.1 |
| 6,555,380 B2 * | 4/2003 | Weinberg | 436/57 |
| 6,736,833 B2 * | 5/2004 | Coleman | 607/94 |
| 7,194,118 B1 * | 3/2007 | Harris et al. | 382/128 |
| 7,374,907 B1 * | 5/2008 | Voneiff et al. | 435/40.52 |
| 7,517,728 B2 * | 4/2009 | Leung et al. | 438/122 |
| 2004/0085443 A1 * | 5/2004 | Kallioniemi et al. | 348/135 |
| 2005/0181033 A1 * | 8/2005 | Dekker et al. | 424/449 |
| 2006/0036182 A1 * | 2/2006 | Daniels et al. | 600/478 |
| 2007/0072258 A1 * | 3/2007 | Chu | 435/40.5 |
| 2009/0217932 A1 * | 9/2009 | Voegele | 128/899 |

* cited by examiner

*Primary Examiner* — Ann Lam
(74) *Attorney, Agent, or Firm* — Martin E. Hsia

(57) ABSTRACT

A process for maintaining 3 dimensional orientation between a tissue specimen and images of the area of investigation, to register histopathologic diagnoses of multiple locations within the specimen with corresponding locations on the surface of said area of investigation.

7 Claims, 17 Drawing Sheets

PROCESS FOR PRESERVING THREE DIMENSIONAL ORIENTATION TO ALLOW REGISTERING HISTOPATHOLOGICAL DIAGNOSES OF TISSUE TO IMAGES OF THAT TISSUE

This application claims the benefit of U.S. Provisional Patent Application No. 61/195,771 filed Oct. 9, 2008.

TECHNICAL FIELD

This invention relates to histopathology analysis and reconstruction and, more specifically, to maintaining the spatial orientation of three-dimensional tissue specimens removed from an area of investigation as an aid in the diagnosis of cancer and pre-cancerous lesions.

BACKGROUND ART

Although this invention is being disclosed in connection with cervical cancer, it is applicable to many other areas of medicine and other fields. Diagnosing cervical cancer in women is a multi-step procedure involving examination of the cervix, possible biopsy and follow-up (D. G. Ferris, J. T. Cox, D. M. O'Connor, V. C. Wright, and J. Foerster, *Modern Colposcopy. Textbook and Atlas*, pp. 1-699, American Society for Colposcopy and Cervical Pathology, 2004; 2. E. Burghardt, H. Pickel, and F. Girardi, *Colposcopy—Cervical Pathology, Textbook and Atlas*, Thieme, New York, 1998, both incorporated herein by reference). It is open to subjective interpretation and dependent upon the skills of cytologists, colposcopists, and pathologists. In a standard colposcopic examination a colposcopist uses a colposcope, which is a low-power, binocular microscope, to visually examine the cervix at a working distance of approximately 300 mm (0.3 cm). Most colposcopes are not digital and do not record images, and records are conventionally kept as hand-drawn representations. While this hand-drawn representation of the cervix is far from adequate, the drawing does provide a limited reference point from which to compare the status of the cervix in future examinations. A significant improvement over the hand-drawing of the cervix would be the use of a video colposcope, or a colposcope with an attached camera, which can capture and provide an image of the cervix.

A colposcopic-directed biopsy is considered the gold standard for diagnosing cervical pre-cancers and cancer, even though it is a subjective assessment with the range of the positive predicted value of colposcopic-directed biopsies being between 36-63% (J. T. Cox, M. Schiffman, and D. Solomon, "Prospective follow-up suggests similar risk of subsequent cervical intraepithelial neoplasia grade 2 or 3 among women with cervical intraepithelial neoplasia grade 1 or negative colposcopy and directed biopsy", American Journal of Obstetrics and Gynecology 188, pp. 1406-1412, 2003, incorporated herein by reference).

Colposcopists are trained to differentiate normal from abnormal tissue with the results of their examination based on their experience and training. Among the cues the colposcopist is looking for are the level of whiteness on the cervix and presence of abnormal blood vessels. The standard procedure is to obtain a specimen sample, via biopsy, from those areas having the highest level of perceived abnormality. These biopsies are then sent for further pathological review. An often undesired result is "false positives," so that unnecessary biopsies are acquired and the specimen is determined normal, which increases the risk of infection, bleeding, physical and emotional discomfort and cost. Furthermore, the decision to treat the patient is based on colposcopic-guided histopathology diagnosis and women with high-grade cervical intraepithelial neoplasia will be referred for more invasive treatment.

In the current practice, biopsies are reviewed by a pathologist, and an overall gross diagnosis of the entire specimen is reported based on the highest level of disease seen. Upon receipt of the pathology report, the colposcopist will know the highest level of disease in the region sampled by the biopsy, not the exact location of the disease within the tissue specimen. Therefore, it is not possible to pinpoint the exact location on the cervix of the reported pathology.

In an effort to reduce the subjective nature of the colposcopist-directed biopsy, and to improve the diagnostic accuracy of colposcopy, new colposcopic imaging systems with accompanying computer aided diagnostic techniques are being developed (as described in co-pending, commonly assigned U.S. patent application Ser. No. 11/895,150, entitled "Uterine Cervical Cancer Computer-Aided Diagnosis (CAD)", filed Feb. 3, 2005, and Ser. No. 12/291,890, entitled "High Resolution Digital Video Colposcope with Built-In Polarized LED Illumination and Computerized Clinical Data Management System", filed Nov. 14, 2008, both incorporated herein by reference) to guide a colposcopist in deciding if and where to biopsy. If the biopsy's histopathology (the identification of the disease state at the cellular and near-cellular level), is to be used as the gold standard for computer aided detection systems, then the location of the histopathology analysis must match exactly to the location of the biopsy tissue in the digital image. Otherwise, no matter how perfect the histopathology and the quality of the digital imagery, the two data sets cannot be matched and the true sensitivity and specificity of the computer aided detection system cannot be determined. In addition, by relying on digital imagery accompanied with the exact location of the histopathologic analysis (instead of hand-drawings of the cervix), the colposcopist is provided with a tool that can reduce the subjective nature of the exam and provide detailed reference data from which to compare the status of the cervix in future examinations.

The present invention includes acquisition, processing, and registration techniques that maintain the spatial orientation at each level of tissue processing of a three-dimensional tissue specimen removed from an area of investigation, perform detailed histopathology analysis, and precisely map the location of the histopathology analysis back to a digital image of the area of investigation (registration) acquired prior to removing the tissue specimen. This is accomplished by utilizing tissue image acquisition, processing, and registration technology in combination with mechanical and image processing tools and novel tissue processing procedures.

The tools and procedures are applied both to the digital image and the actual tissue specimens that are removed. One tool, the macrotome, adds precision to the orientation and overall size of tissue specimen blocks in preparation for routine slicing and microscope slide mounting. Another tool, the needle guide, permits the application of needle tracks at the interior of the tissue specimen which ensures accurate alignment of the histopathology tissue slices. Other tools include the use of standard imaging devices and annotation software, in which prepared microscope slides are digitally scanned, reviewed and annotated by a pathologist for diagnostic and orientation features.

In addition to providing the overall gross diagnosis for the entire specimen of the current pathology practice, the current invention provides a detailed histological analysis which, by applying image registration tools, can subsequently be mapped back to the digital imagery of the area of investigation. This reconstructed histopathology map will then provide the gold standard for colposcopy assessment and computer aided detection systems.

The current invention has the potential to raise the level of expertise of a more junior colposcopist to that of the more experienced colposcopist resulting in possible improvements in the identification of disease and early stage lesions. The invention could also reduce the diagnostic noise of inflammation and other conditions that interfere with the proper identification of pre-cancer and cancer, as well as minimizing the number of unnecessary biopsies.

By combining the objective accuracy of tissue classification using computer aided detection algorithms with the orientation properties of the tissue specimen processing of the current invention and digital slide annotations, each slide can be registered with its corresponding colposcopic image and show on a linear level where the disease is on the cervix and what level of disease is present. This has the potential to be able to direct a colposcopist to a more exact location for acquiring a biopsy. It could also provide a map for any follow-on surgical steps, enabling the physician to make smaller treatment excisions because the extent and location of the lesion can be determined more precisely.

The presently preferred embodiments of the invention described herein comprise a systematic framework for maintaining the spatial orientation of a three-dimensional tissue specimen removed from an area of investigation. The following patents and patent applications may be considered relevant to the field of the invention:

U.S. Pat. No. 1,859,467 to Rath, incorporated herein by reference, discloses means and methods for identifying products as to their particular origin, and which consists in making such structural changes in a product that it will possess a physical characteristic of any desired nature, and of a persistent kind, symbolic of a certain origin or derivation, to afford means for identifying the product with the producer, whether the latter is classed as a grower, manufacturer, processor, or seller thereof.

U.S. Pat. No. 2,868,072 to Weiskopf et al., incorporated herein by reference, discloses a mounting device for a paraffin-blocked histologic tissue specimen adapted for mounting to the specimen holder of a microtome.

U.S. Pat. No. 4,276,253 to Adler, Sr., et al., incorporated herein by reference, discloses a method for labeling a histological specimen, wherein such specimen is embedded in a paraffin block along with an integral set of supported elongated elements identifying such specimen for subsequent sectioning on a microtome. The identification elements are sectioned concurrently with the specimen, so as to form an integral part of the section.

U.S. Pat. No. 4,569,647 to McCormick, incorporated herein by reference, discloses an apparatus for the simultaneous preparation of multiple tissue specimens for histological examination, comprising cooperating stackable capsules, each of said capsules including a mold member and a complementary removable cover member.

U.S. Pat. No. 4,695,339 to Rada, incorporated herein by reference, discloses a system for preparing frozen tissue blocks for sectioning in a microtome. A vacuum-retracted membrane of plastic film material is used to draw a tissue block or specimen into planar contact with a polished platform that is positioned in a vacuum receptacle assembly.

U.S. Pat. No. 4,752,347 to Rada, incorporated herein by reference, discloses a method and apparatus for preparing a tissue block for sectioning in a microtome. A vacuum-retracted membrane of plastic film material is used to draw an underside of the tissue block or specimen into planar contact with a platform. The tissue block is frozen on the platform once it is properly oriented. The membrane is subsequently peeled away from the platform and O.C.T. compound is applied to the tissue blocks. The O.C.T. compound (after hardening) and the tissue block are transferred to a second platform carried by a mounting device such that the tissue underside is exposed. The tissue specimen is ready for sectioning as part of the Mohs fresh tissue surgical technique.

U.S. Pat. No. 4,893,424 to McLean, incorporated herein by reference, discloses a method and apparatus for permanently identifying an individual tissue sample sectioned for microscopic examination, as well as for identifying a tissue sample throughout the entire treatment cycle, including sectioning for mounting on slides.

U.S. Pat. No. 5,082,254 to Hunell et al., incorporated herein by reference, discloses a microtome object holder clamping assembly, having utility for positioning a ball-mounted specimen plate in a spatially fixed manner, but which is selectively repositionable by pivotal and/or rotational movement to dispose the specimen plate at any desired orientation relative to the microtome knife element. The microtome object holder clamping assembly of the invention may be usefully employed in a variety of microtome structures, including microtome cryostats, for sectioning of selected specimens.

U.S. Pat. No. 5,550,033 to Krumdieck, incorporated herein by reference, discloses a method and apparatus for preparing tissue samples for subsequent slicing in a microtome, utilizing a thermally transmissive body and removable mold heads to facilitate encapsulation of tissue samples in a gelatinous substance so that the samples may be selectively oriented for proper slicing in the microtome.

U.S. Pat. No. 6,017,476 to Renshaw, incorporated herein by reference discloses a specimen processing method which enables a specimen to be embedded in exactly the same plane as the cutting plane of a microtome during sectioning. This minimizes the number of sections required for histologic evaluation and eliminates the need for mechanical handling of the tissue specimen after its initial collection.

U.S. Pat. No. 6,387,653 to Voneiff et al., incorporated herein by reference, discloses an apparatus and method for producing tissue slides. The apparatus includes a holding assembly for manipulating the sample block, a blade assembly for preparing a thin section from the sample block, and a transfer roller mechanism for transferring the thin section to a receiving medium. The apparatus further includes a controller that may track the sample block and thin section.

U.S. Pat. No. 6,558,629 to Davidson, incorporated herein by reference, disclose a receptacle and dipping assembly aid in the preparation of a tissue sample for frozen histologic sectioning.

U.S. Pat. No. 7,005,110 to Taft et al., incorporated herein by reference, discloses a method to prepare tissue samples for sectioning comprising embedding a tissue sample in a porous embedding media in a desired orientation, followed by processing, and sectioning, all while being held in the porous embedding media. The post-tissue processing step of manual embedding in paraffin is eliminated from the process.

U.S. Pat. No. 7,029,615 to Lilischkis et al., incorporated herein by reference, discloses a method for the production of a material block containing a number of test samples, particularly tissue samples, a material blank, preferably made of paraffin and containing a number of openings to accommodate the corresponding tissue samples.

U.S. Pat. No. 7,168,694 to Bui et al., incorporated herein by reference, discloses a multi-axis chuck that rotates about at least two axes.

U.S. Pat. No. 7,257,953 to Rada, incorporated herein by reference, discloses apparatus and method for rapidly freezing tissue specimens at cryogenic temperatures that enhances heat transfer, quickly cools tissue holders and tissue, facilitates cutting of thin tissue sections, and facilitates tracking of tissue specimens throughout a tissue preparation and examination process.

U.S. Pat. No. 7,357,384 to Thiem, incorporated herein by reference, discloses a device for signaling the position of an orientable sample holder for a microtome.

U.S. Pat. No. 7,405,056 to Lam et al., incorporated herein by reference, discloses methods, devices, and systems using labeled punch tubes in the preparation of tissue microarrays and microarray slides, for tissue sample archiving, for correlating pathology, histology, and other biological test results with specific source tissues through intermediary tissue configurations.

U.S. Patent Application Number 2004/0018264 to Graziano et al., incorporated herein by reference, discloses a device and a method for sectioning of organs and irregular tissue blocks into tissue sections of a predefined thickness and orientation, in one uniform working process. The tissue is embedded into an alginate polymer, which is poured into an embedding container with two opposite arrays of parallel grooves. After hardening, the polymer is sectioned in slices of a predetermined thickness. This is achieved by razor blade cuts through an array of parallel grooves in the embedding container. The tissue and alginate polymer are then removed by removing the side of the embedding container, resulting in a series of parallel sections of predefined and often equal thickness.

U.S. Patent Application Number 2005/0112032 to McCormick, incorporated herein by reference, discloses a histological specimen retaining device for processing tissue, the device comprising: a foldable permeable sheet having edges; a permeable target disposed on the foldable permeable sheet within the edges of said sheet, thereby providing extended flap portions which flap portions are foldable to overlap the target; and a malleable securing strip attached to the foldable permeable sheet of a length sufficient to secure said folded flap portions overlapping said target.

U.S. Patent Application Number 2005/0112034 to McCormick, incorporated herein by reference, discloses a system for use in the preparation in situ of tissue specimens for histological examination. The invention also is directed to a method of processing a tissue sample for histological examination which does not require re-orienting the selected cutting plane in the specimen transfer step. Instead, the tissue sample remains oriented in a desired position throughout processing.

U.S. Patent Application Number 2007/0172942 to Walter et al., incorporated herein by reference, discloses an apparatus for producing a tissue array, the apparatus comprising: a donor block including tissue to be investigated, a specimen slide on which is provided a marked tissue section of the tissue to be investigated; a hollow needle for removing a sample from the donor block, and a sighting device connected to the hollow needle for positioning the hollow needle above the donor block.

U.S. Patent Application Number 2007/0184430 to Niendorf et al., incorporated herein by reference, discloses a method of analyzing a patient tissue sample to determine its diseased tissue fraction while essentially preserving the genomic and/or proteomic and/or epigenomic and/or biophysical properties of the tissue sample.

U.S. Patent Application Number 2007/0196891 to McCormick, incorporated herein by reference, discloses a histological specimen retaining device for processing tissue, the device comprising: a foldable permeable sheet having edges; a permeable target disposed on the foldable permeable sheet within the edges of said sheet, thereby providing extended flap portions which flap portions are foldable to overlap the target; and a malleable securing strip attached to the foldable permeable sheet of a length sufficient to secure said folded flap portions overlapping said target.

European Patent Number EP 1842044 to McCormick, incorporated herein by reference, discloses a system for use in the preparation in situ of tissue specimens for histological examination. The invention also is directed to a method of processing a tissue sample for histological examination which does not require re-orienting the selected cutting plane in the specimen transfer step. Instead, the tissue sample remains oriented in a desired position throughout processing.

Japan Patent Number JP 10333051 to et al., incorporated herein by reference, discloses a method to place a sample slice on a slide glass with reference at a sample slice positioning mark and to make a placing position definite by putting the sample slice positioning mark at the transparent part except the frost part of the slide glass.

International Patent Application PCT/AU1994/000715 to Muir et al., discloses a cassette for tissue specimen processing with removable top and bottom.

International Patent Application PCT/US1996/009676 to Casparian, incorporated herein by reference, discloses a method of optimizing gross tissue for pathological analysis, including positioning and orientation, comprising the steps of: contacting said tissue with a rigid, flat device, said device bearing on one surface at least one temperature sensitive adhesive component; and performing a pathological analysis International Patent Application PCT/US2005/042933 to McCormick, incorporated herein by reference, discloses a system for use in the preparation in situ of tissue specimens for histological examination. The invention also is directed to a method of processing a tissue sample for histological examination which does not require re-orienting the selected cutting plane in the specimen transfer step. Instead, the tissue sample remains oriented in a desired position throughout processing.

DISCLOSURE OF THE INVENTION

The invention is a process for maintaining 3 dimensional orientation between a tissue specimen excised from an area of investigation, and images of the surface of the area of investigation, so that histopathologic diagnoses of multiple locations within the specimen can be registered with corresponding locations on the surface of the area of investigation, as follows:

acquiring a reference image of the surface of the area of investigation;

marking at least two fiduciary lines on tissue of the area of investigation at appropriate positions as not to obscure or destroy diagnostically significant information;

acquiring a fiduciary image of the surface of the tissue with the fiduciary lines;

excising the tissue to form the tissue specimen;

inserting at least two parallel needles through the specimen;

acquiring a specimen image of the specimen and the inserted needles over an alignment grid;

fixing the specimen to form a fixed specimen;

acquiring a fixed image of the fixed specimen and the inserted needles over the alignment grid;

forming a paraffin mold containing the fixed specimen and the inserted needles;

injecting different colored inks through the needles while withdrawing the needles from the fixed specimen, whereby different colored needle tracks are formed in the specimen;

sectioning the specimen to create specimen blocks having the different colored needle tracks;

further sectioning the specimen to cut the specimen blocks into specimen slices having different colored ink dots corresponding to the different colored needle tracks, whereby the different colored ink dots serve as reference points;

forming pathology images from the specimen slices;

performing histopathology analyses on the pathology images;

annotating the pathology images with histopathology annotations;

aligning the annotations with the fixed image using the reference points;

determining shrinkage between the fixed image and the annotations by comparing the distance between the needles on the grid in the fixed image with the distance between the reference points on the specimen slices in the pathology images;

registering the fixed image to the specimen image to account for shrinkage caused by fixation, by using locations of the needles in both of the images as landmarks; and registering the specimen image to the fiduciary image to account for tissue translation and soft tissue movement using the fiduciary lines and geographical features of the area of investigation as landmarks;

registering the fiduciary image to the reference image to account for tissue translation and soft tissue movement using the geographical features;

whereby annotations of histopathologic diagnoses are provided for multiple locations on or under the surface of the specimen that are shown in the fiduciary image of the specimen.

The inserting step can be performed with three parallel needles.

The fixing step can be performed by immersing the specimen and inserted needles in a fixing material selected from the group consisting of formaldehyde, tannic acid, glutaraldehyde, tannic acid, picric acid, absolute alcohol, potassium dichromate, mercuric chloride and osmium tetroxide.

The fixing step can be performed by rapid heating or quick freezing the specimen and inserted needles.

Where specimen slices for analysis can be obtained directly, without initial sectioning to create specimen blocks, the invention provides a process for registering histopathologic diagnoses of multiple locations within a tissue specimen from an area of investigation with corresponding locations on the surface of the area of investigation by maintaining three dimensional orientation between the specimen and the surface of the area of investigation. This is done by marking fiduciary lines on tissue of the area of investigation;

acquiring a fiduciary image of the area of investigation and the fiduciary lines;

excising the tissue to form the tissue specimen;

inserting at least two parallel needles through the specimen;

acquiring a specimen image of the specimen and the inserted needles over an alignment grid;

forming at least one colored needle track in the specimen using the needles;

sectioning the specimen into specimen slices having at least one colored ink dot corresponding to a colored needle track, whereby the colored ink dot and an uncolored dot corresponding to any uncolored needle tracks serve as reference points;

performing histopathology analyses on the specimen slices;

annotating pathology images of the specimen slices with histopathology annotations;

registering the annotations with the specimen image using the reference points;

determining shrinkage between the specimen image and the annotations by comparing the distance between the needles on the grid in the specimen image with the distance between the reference points; and registering the specimen image to the fiduciary image using the fiduciary lines and geographical features of the area of investigation as landmarks;

whereby annotations of histopathologic diagnoses are provided for multiple locations on or under the surface of the area of investigation that are shown in the fiduciary image.

In its broadest aspect, the invention provides a process for maintaining three dimensional orientation between a tissue specimen from an area of investigation with corresponding locations on the surface of the area of investigation, comprising:

marking fiduciary lines on tissue of the area of investigation;

acquiring a fiduciary image of the area of investigation and the fiduciary lines;

excising the tissue to form the tissue specimen;

forming parallel needle tracks in the specimen by inserting at least two parallel needles through the specimen;

coloring at least one of the needle tracks to form at least one colored needle track;

acquiring a specimen image of the specimen and the inserted needles over an alignment grid; and sectioning the specimen into specimen slices having at least one colored ink dot corresponding to the at least one colored needle track and an uncolored dot corresponding to any uncolored needle track, whereby the at least one colored ink dot and any uncolored dot serve as reference points;

whereby images of the specimen slices can be registered to the specimen image using the reference points, and the specimen image can be registered to the fiduciary image using the fiduciary lines and geographical features of the area of investigation as landmarks. Thus, the broadest aspect of the invention allows, for example, registering images of the specimen slices (tomographic images) against images of the area of investigation. One or more of the needle tracks can be colored as the needles are inserted (or afterwards) rather than as the needles are withdrawn, or in some other manner.

Indeed, the tracks can be formed using other means, such as a laser or drill, as long as the tracks can be viewed in subsequent images over an alignment grid, such as with X-rays, microwaves, infra red, MRI, or other imaging techniques (so that "colored" ink includes ink that is visible using such imaging techniques, even if not colored in visual light). This technique therefore could also be used with materials other than human, plant and animal tissue, such as with geological or other samples of inorganic materials taken from an area of investigation, for which registering tomographic (slice by slice) information to the surface of the material and the area of investigation may be desired.

A separate reference image of the area of investigation, free of the fiduciary lines, may not be necessary, to preserve storage space (for example). A fixing material that does not cause shrinkage may be employed, so that determining shrinkage may not be necessary.

The slicing of specimen blocks having different colored needle tracks to form specimen slices having different colored dots allows for maintaining spatial orientation of a three-dimensional tissue specimen removed from an area of investigation. However, it may not be necessary to form specimen blocks before forming specimen slices, as specimen slices can be taken directly from the specimen. The fiduciary lines placed at the time of tissue excision, and the internal needle tracks, along with the precise slices of tissue at exacting intervals allows for the "z-axis" histology to accurately "underlie" the x and y axes. In order to perform the functions of preserving orientation and determining shrinkage, marks in the specimen must be part of the tissue, be inserted as soon as the tissue is excised, and be part of the specimen throughout the entire tissue processing. Marks that are only added after fixation and resulting dehydration cannot be used to determine and compensate for orientation and shrinkage. Further, if the marks are made with material having properties different from the properties of the sample, then such marks may not allow accurate restoration to compensate for orientation and shrinkage.

This ability to maintain spatial orientation at each level of tissue processing and accurately determine the location of the tissue slice as it relates to the overlying tissue photographed prior to tissue excision allows the subsequent histopathologic diagnoses to be annotated to the surface of each slice of the specimen, and mapped to the appropriate overlying x-y axis points. This becomes especially important when assigning topographic characteristics of the colposcopic appearance of the cervix in the two-dimensional (x-y) plane provided by the colposcopic photography immediately preceding the tissue excision. It also can become important in the evaluation of hyperspectral imaging as it relates to the spectrum of light emitted from the cervix following application of acetic acid. In essence, this method of tissue processing from the moment the tissue specimen leaves the body, to the point where annotations of the histopathologic "linear diagnosis" is rendered along each micron of the surface will allow the most accurate assignments of z-axis to the overlying x-y plane of the original sample "in situ".

BRIEF DESCRIPTION OF THE DRAWINGS

FIG. 2 is illustrations of digital cervical images.

FIG. 6 is a illustration of the placement and alignment of the tissue specimen in the needle guide tool.

FIG. 7 is an illustration of the needle insertion process using the needle guide tool.

FIG. 8 is an illustration of the tissue specimen with needles on the grid and alignment pattern of the needle guide tool.

FIG. 9 is illustrations of tissue specimen images before and after the application of a fixing agent, such as formaldehyde, to fix the specimen.

FIG. 10(A) shows the tissue specimen and needles in the paraffin mold.

FIG. 12 is an illustration of the macrotome cutting process.

FIG. 13 is an illustration of radial versus parallel cutting of a tissue specimen.

FIG. 14 is an illustration of the microtome procedure.

FIG. 17 is an illustration of the different steps in back correlating the histopathology annotations to the fixed image.

BEST MODE FOR CARRYING OUT THE INVENTION

Overview

The presently preferred embodiments of the invention described herein disclose a systematic framework to maintain the spatial orientation at each level of tissue processing of a three-dimensional tissue specimen removed from an area of investigation, perform detailed histopathology analysis, and precisely map the location of the histopathology back to a digital image of the area of investigation acquired prior to removing the tissue specimen.

Figure 1:
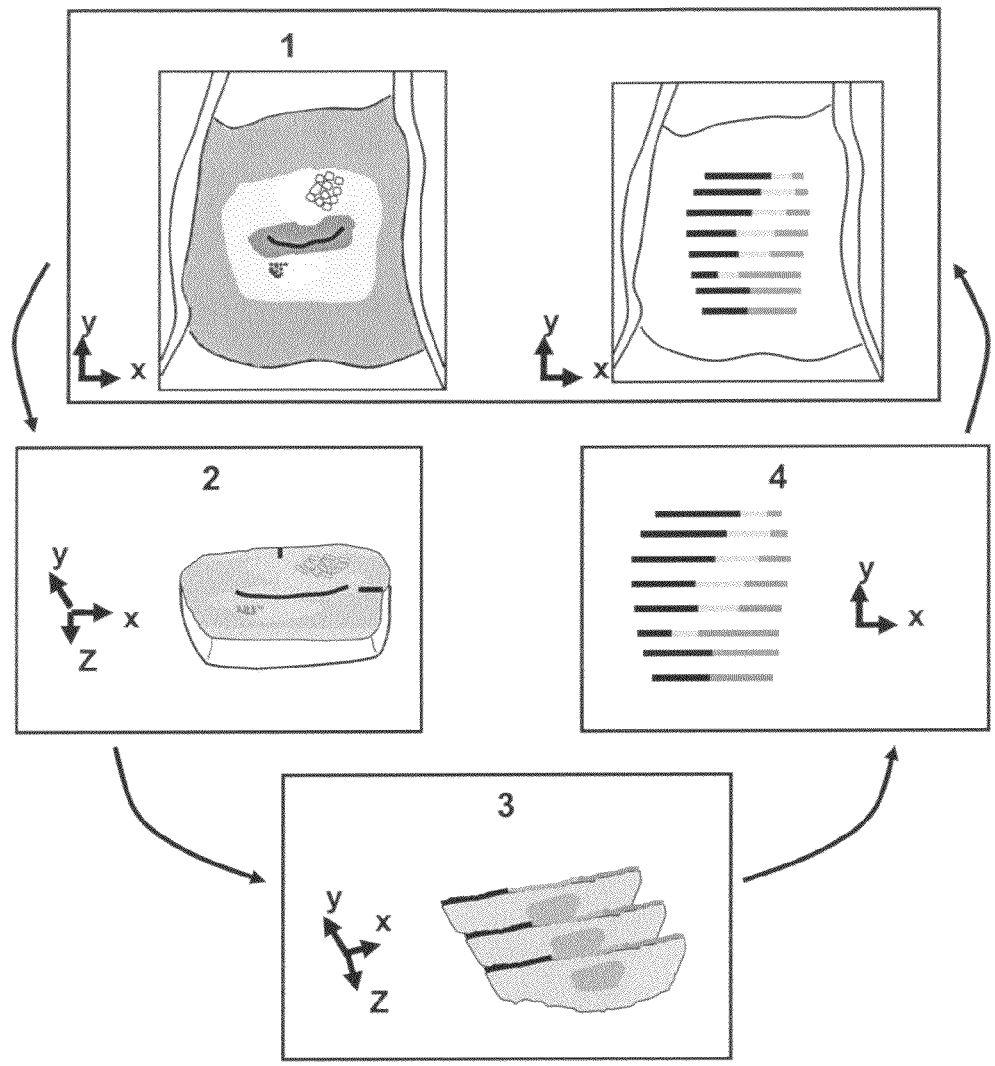
FIG. 1 is a schematic illustration of the procedural steps of the present invention including (1) Tissue image acquisition, (2) Tissue specimen processing, (3) Histopathology processing, and (4) Histopathology reconstruction. The coordinate system (x-y-z) is illustrated for each step.

By utilizing tissue image acquisition, processing, and registration techniques in combination with mechanical and image processing tools and novel tissue processing procedures, the present invention accurately determines the location of the histopathology analysis (the 'z-axis') of the tissue specimen as it relates to the overlying tissue structure (the 'x-y-axes'). The procedural steps of the presently preferred embodiments, as schematically illustrated in FIG. 1, and which will be described in detail in the following sections, are summarized as follows:

1. Tissue image acquisition: A digital reference image or images of the area of investigation are captured and saved. The surface of the area of investigation in the digital image defines the two-dimensional, x-y, plane.
2. Tissue specimen processing: A tissue specimen is removed from the areas of investigation and processed by mechanical and image processing tools to maintain the orientation of the tissue sample relative to the reference image. The depth of the tissue sample defines the z-axis.
3. Histopathology processing: Tissue slices are generated and histopathology annotations are performed. The surface of the tissue slices defines the x-axis, the position of the slices in the tissue sample sets the y-axis, and the depth is aligned with the z-axis.
4. Histopathology reconstruction: By meticulously maintaining the orientation of the tissue sample and slices relative to the reference image, the histopathology annotations are precisely back correlated to and overlaid on the reference image.

1. Tissue Image Acquisition

At the clinical site during the clinical examination, at least one image of the tissue under investigation is acquired. This image is hereafter referred to as the reference image. Depending on the application, additional images can be acquired. For example, in colposcopy, one image of the cervix is usually acquired at the beginning of the colposcopic procedure. Following the application of acetic acid solution, another image of the cervix is usually acquired. In the presently preferred embodiment, this image acquired after the application of acetic acid is referred to as the reference image. The reason for applying acetic acid in colposcopy is that virtually all cervical neoplasias display a variably transient and opaque white color following the application and, as such, this acetowhite epithelium can be used to predict the severity of cervical lesions. In some colposcopic examinations, Lugol's iodine solution is applied and a third image is acquired. The reason for applying Lugol's iodine in colposcopy is that after the application, normal cervical tissue typically stains brown while tissue suspicious for cervical neoplasia does not stain and, thus, appears pale compared to the surrounding tissue. Illustrations of colposcopic images acquired before and after application of acetic acid, as well as after the application of Lugol's iodine is presented in FIG. 1. The surface of the cervix defines the two-dimensional, x-y, plane of the area of investigation.

Figure 3:
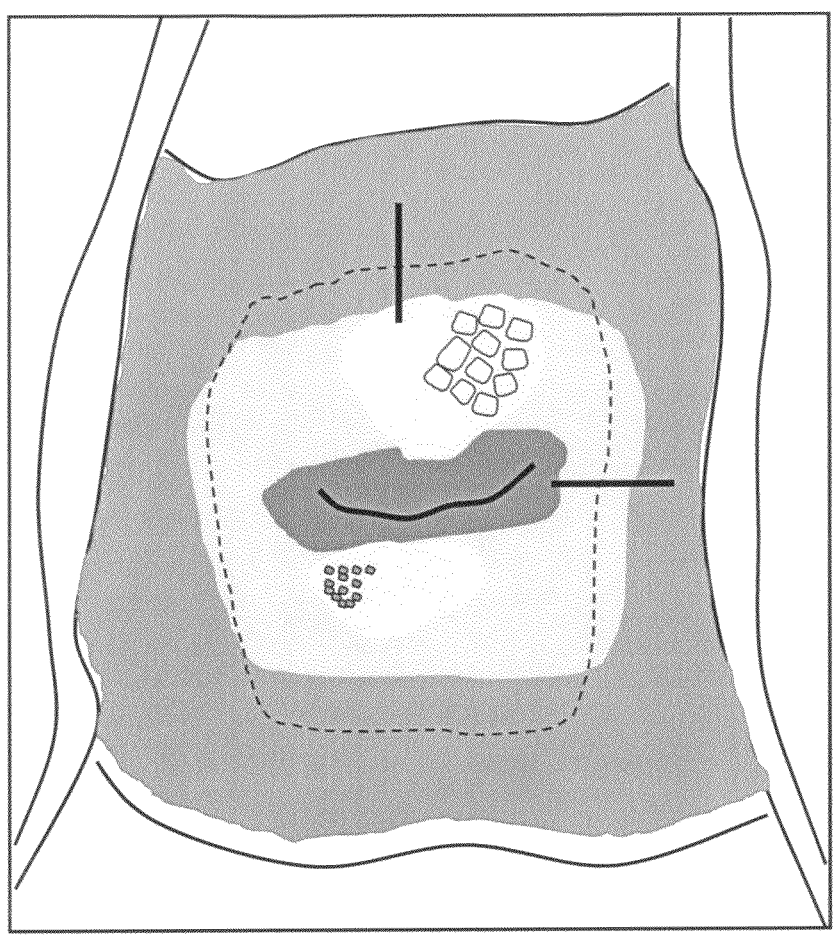
FIG. 3 is an illustration of a fiduciary image with fiduciary lines at 12 and 3 o-clock. The outline of the tissue specimen excision is shown as a dotted line.

Before the tissue specimen is excised, the area of investigation is marked with at least two fiduciary lines (these fiduciary lines can be any markings, not just straight lines), at appropriate positions as not to obscure or destroy diagnostically significant information such as a pre-cancerous lesion (note that in other applications besides cervical cancer, the entire organ may be removed and be the tissue specimen, such as the prostate). To maintain the orientation of the tissue specimen, one of the fiduciary lines is preferably located at the 12 o'clock position; the other fiduciary line at either 3, 6 or 9 o'clock position. An image of the area of investigation with the fiduciary lines is then acquired. This image, hereafter referred to as the fiduciary image, is schematically illustrated in FIG. 3. The fiduciary lines can be made with any marker that adheres to tissue and does not smear upon application, such as a surgical marker. If smearing occurs, the exact location of the fiduciary lines cannot be ascertained and the performance of any registration algorithm applied in later stages on the present invention will be diminished. In colposcopy, the fiduciary lines can be burn marks applied using the standard tool used during loop electrosurgical excision procedures (LEEPs). The fiduciary lines should be made long enough so that part of the line will be on the excised tissue specimen with the remaining portion of the line on the tissue that remains on the area of investigation after tissue specimen excision (see FIG. 3).

2. Tissue Specimen Processing

Figure 4:
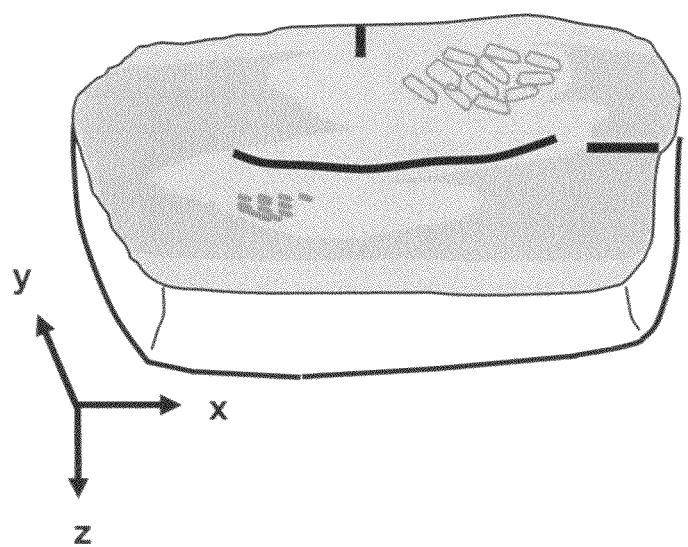
FIG. 4 is a schematic illustration of an excised tissue specimen with fiduciary lines at 12 and 3 o'clock. A coordinate system (x-y-z) indicates the three-dimensional properties of the tissue specimen.

After the application of the fiduciary lines, the tissue specimen is excised using the appropriate surgical tool. For example, in colposcopy a LEEP, cold knife conization, or laser conization tools are preferably used. A sample tissue specimen is displayed in FIG. 4, illustrating the x-y plane of the tissue surface, the z-axis along the depth of the tissue specimen, and the fiduciary lines on the surface of the tissue specimen.

Following excision, the tissue specimen is processed through a needle guide tool in which the tissue specimen has parallel needles inserted, is measured and photographed. The needle guide is designed to provide a set of internal reference points, intended to allow more precise alignment of the z-axis, or depth of the tissue specimen, to the overlying x and y axes, as given by the image of the tissue surface. However, if more than two needles are used, it is not necessary that they all be coplanar, as they can be parallel and not coplanar, so as to form needle tracks that are not co-linear, but are the same in cross section throughout the specimen, forming a triangle, square or other shape. Of course, it is also possible to practice the invention with needles that are not even parallel, but this is not preferred, because it would make aligning slices (see below) much more complex.

Figure 5:
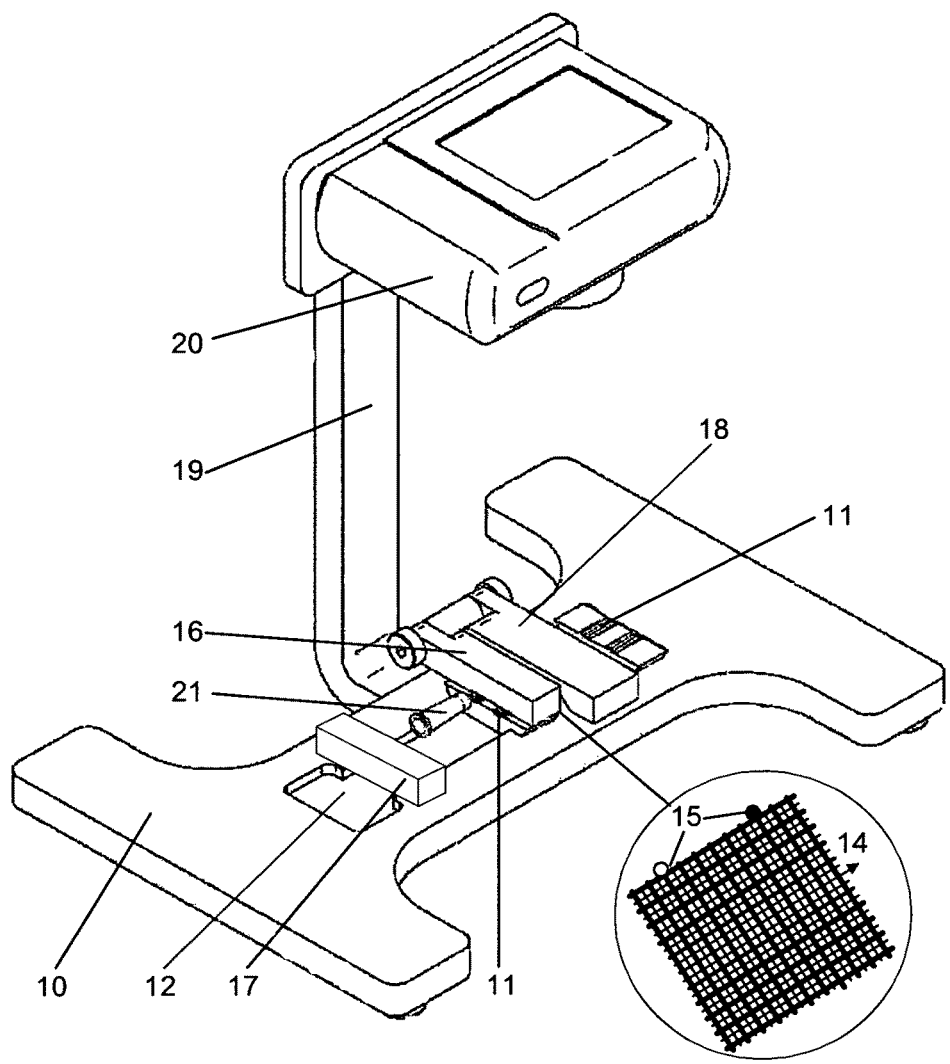
FIG. 5 is a perspective view of the needle guide tool.

The needle guide is shown in FIG. 5. The needle guide includes the base plate 10 which includes a number of grooves 11 in which needles 21 can be placed and aligned, a cut out 12 perpendicular to the needle grooves 11 to facilitate the movement of the needles 21 between the grooves 11, a grid and alignment pattern 14 and alignment pins 15 to facilitate measuring the size of and aligning the tissue specimen. The exact size and dimension of the grid and alignment pattern depends on the application and size of the tissue specimen. For cervical tissue samples, the grid and alignment pattern preferably covers 30 mm by 30 mm and has a grid distance of 1 mm. The needle guide also preferably includes a needle clamp 16 to prevent the needles 21 from wandering as they are driven forward and through (preferably completely through) the tissue specimen. The needle rake 17 is used to push the needles through the tissue specimen and a tissue specimen clamp 18 is employed to keep the tissue specimen from moving as the needles are pressed through the tissue specimen. The needle guide also includes a digital image acquisition device 20, which is attached to the base plate with a bracket 19. The digital image acquisition device 20 is positioned directly above the grid and alignment pattern to capture images of the tissue specimen along with the grid pattern.

At present, preferably, two needles are used. However, optionally more needles can be used. For example, three parallel needles can be used in order to detect and compensate for bending of a specimen.

Figure 6A:
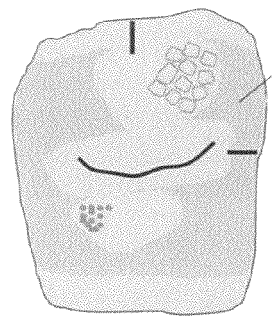
FIG. 6(A) shows the face up image of the tissue specimen.
Figure 6B:
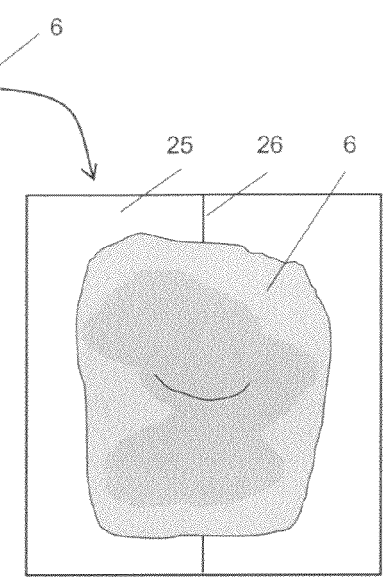
FIG. 6(B) show the face down image of tissue specimen aligned on the glass slide.
Figure 6C:
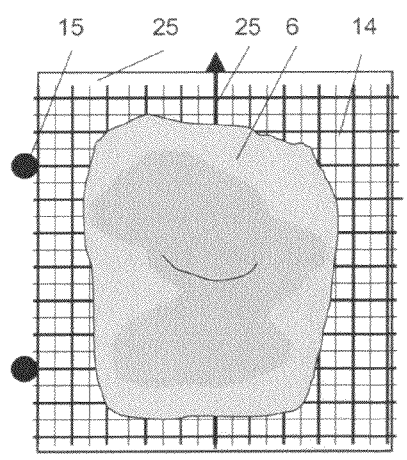
FIG. 6(C) shows the tissue specimen and glass slide aligned on the grid and alignment pattern.

The fresh tissue specimen 6 (see FIG. 6(A)) is flipped and placed face down on a glass slide having an alignment groove 26 (see FIG. 6(B)). To maintain the orientation of the tissue specimen 6, one of the fiduciary lines is preferably aligned with the alignment groove 26. The glass slide 25 with the tissue specimen 6 is in turn placed on the grid and alignment pattern 14 and pushed against the alignment pins 15 which ensure that the alignment groove 26 of the glass slide 25 is aligned with the center line of the grid and alignment pattern 14 (see FIG. 6(C)). This face down procedure ensures that the needles are always inserted at a pre-determined depth relative to the tissue surface.

Figures 7A, 7B:
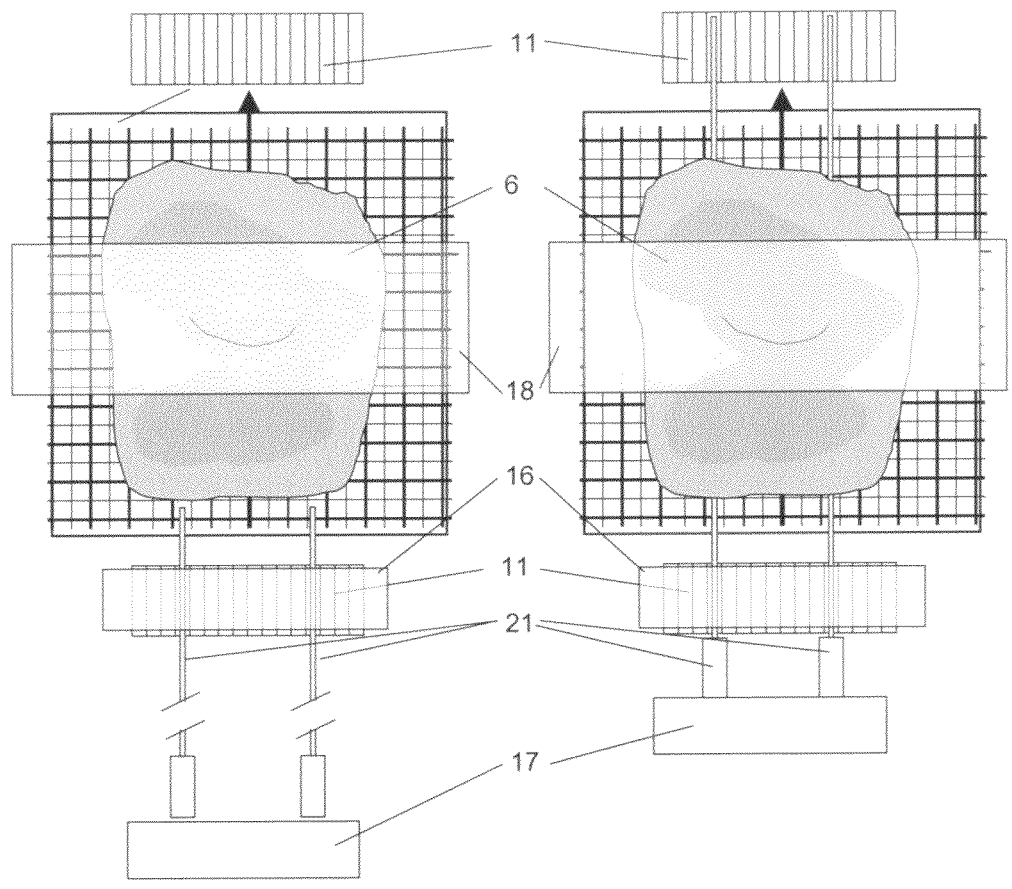
FIG. 7(A) shows the needles aligned prior to insertion.
FIG. 7(B) show the needles pushed parallel through the tissue specimen.

At least two disposable needles 21 are placed into the grooves 11 of the needle guide as shown in FIG. 7(A). The positions of the needles 21 are adjusted such that they both pass through the entire length of the tissue specimen while at the same time do not go through holes of the tissue specimen. The latter is especially important for cervical tissue specimens which include an area with no tissue, the cervical os. The needle clamp 16 and specimen clamp 18 are attached and the needle rake 17 is used to push the needles, in parallel, through the tissue specimen as illustrated in FIG. 7(B).

Figure 8A:
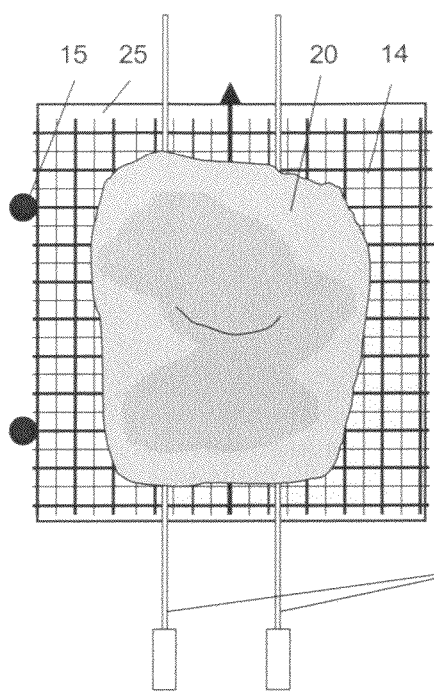
FIG. 8(A) shows the face down position of the tissue specimen and the needles.
Figure 8B:
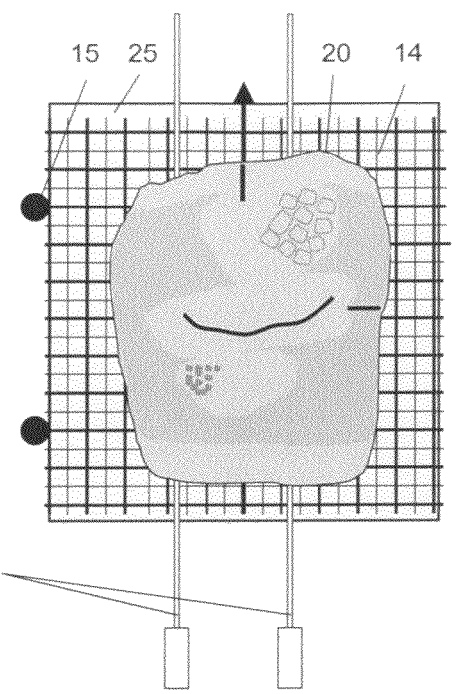
FIG. 8(B) shows the face up of the tissue specimen and the needles.
Figure 9A:
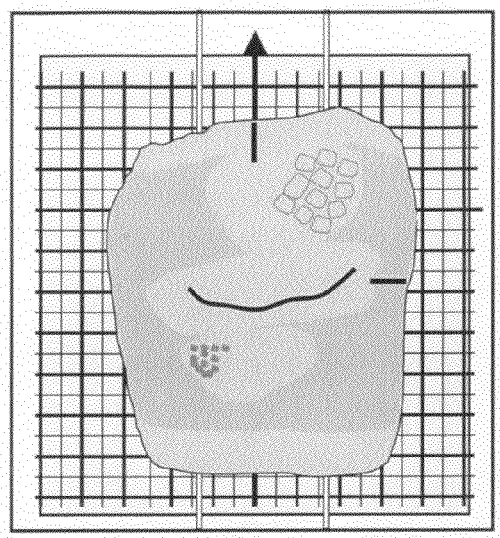
FIG. 9(A) shows the specimen image.

The tissue clamp 18, needle clamp 16 and rake 17 are removed from the needle guide. The tissue specimen 6 with the parallel needles 21 (see FIG. 8(A)) is flipped over and placed face up on the glass slide 25 (see FIG. 8(B)) and, again, oriented such that the center of one of the fiduciary lines is aligned with the alignment grove 26 on the glass slide 25. An image of the tissue specimen, needles, and reference dimensions provided by the grid and alignment pattern is acquired. This image, hereafter referred to as the specimen image, is illustrated in FIG. 9(A).

The tissue specimen with the parallel needles is removed from the needle guide, placed in a sample jar, and backfilled with a material to fix the image, preferably formaldehyde. Formaldehyde is used in the preferred embodiment because it remains liquid and does not plug the needles. However, any fixing material that does not plug the needles can be used, such as tannic acid, glutaraldehyde, tannic acid, picric acid, absolute alcohol, potassium dichromate, mercuric chloride and osmium tetroxide. The specimen can also be fixed using physical methods, such as rapid heating of quick-freezing.

Figure 9B:
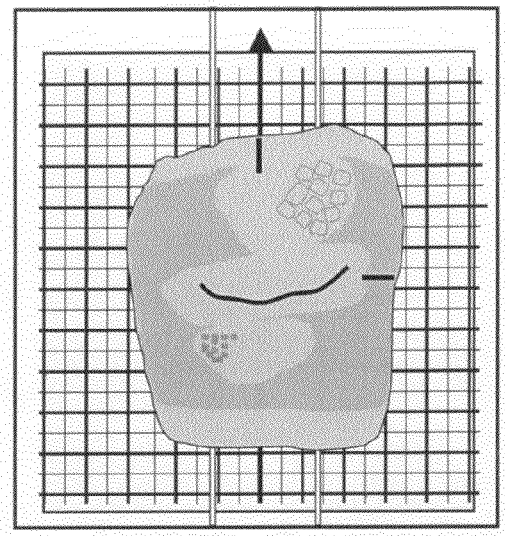
FIG. 9(B) shows the fixed image.

The tissue specimen with the needles is removed from the jar and placed face up such that the center of one of the fiduciary lines is aligned with the grid and alignment pattern. An image of the tissue specimen and needles with the grid and alignment pattern is captured in order to measure the shrinkage artifact caused by formalin fixation. This image, hereafter referred to as the fixed image, is illustrated in FIG. 9(B).

Figure 10:
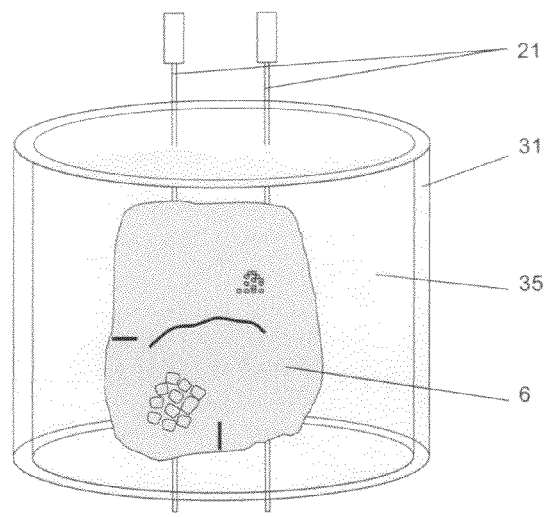
FIG. 10 is an illustration of aligning the tissue specimens with needles in a paraffin mold and the injection of different color inks into the tracks of the needles.
Figure 10B:
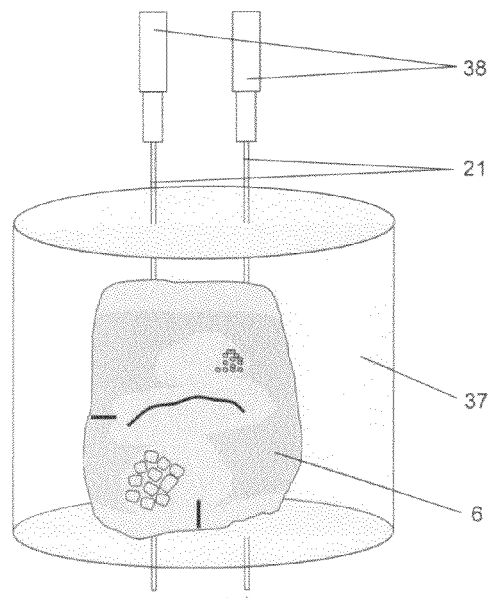
FIG. 10(B) shows the attachment of the syringes with different color inks.
Figure 10C:
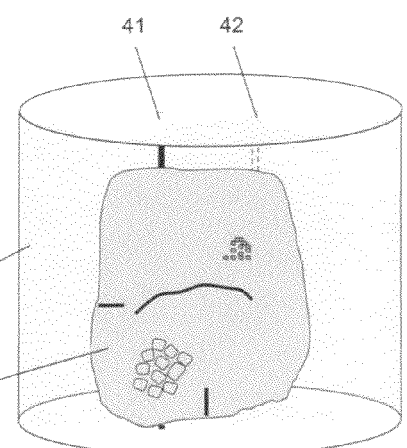
FIG. 10(C) shows the needles removed and the different color inks in the tracks of the needles.

The formaldehyde fixated tissue specimen 6 with the parallel needles 21 is then placed into a cylinder mold 31 as illustrated in FIG. 10(A). The needle points are preferably slightly embedded in the bottom of the mold to hold the tissue specimen and needles vertically aligned, and to ensure that the top of the tissue specimen rests on the bottom of the mold. The cylinder mold is backfilled with paraffin 35 which is allowed to harden and dry. The hardening can be accelerated by cooling the mold and placing the entire device in a refrigerated environment. The paraffin mold 31 with the tissue specimen 6, the parallel needles 21, and the paraffin 35, is then removed from the cylinder mold 31. Syringes 38 containing different color inks are attached to the hub of the needles 21 (see FIG. 10(B)) and injected as the needles 21 are extracted from the paraffin mold 37. Once the needles are removed (see FIG. 10(C)), different color inks are left along the wall of the holes left by the needles; one color ink 41 for the right injection site and another color ink 42 for the left injection site. An alternative embodiment would be to use ink for one hole only and leave the other hole without ink. Indeed, ink is not necessary if (a) three or more non-coplanar needle or other tracks are formed through the specimen so that the resulting dots in each slice form an asymmetric polygon; or (b) a single needle or other track is formed in the shape of an asymmetric polygon (although this may not allow correcting for shrinkage).

The paraffin mold 37 with the tissue specimen 6 and the parallel needle marks is then processed through a macrotome tool to create tissue specimen block 7 of a precise thickness and at a known depth in the oriented tissue specimen. The macrotome tool provides precise alignment of the x-y plane of the tissue specimen along the z-axis which is another crucial step in maintaining referential integrity of the overlying reference tissue image and underlying histology eventually annotated on digital histopathology slides.

Figure 11:
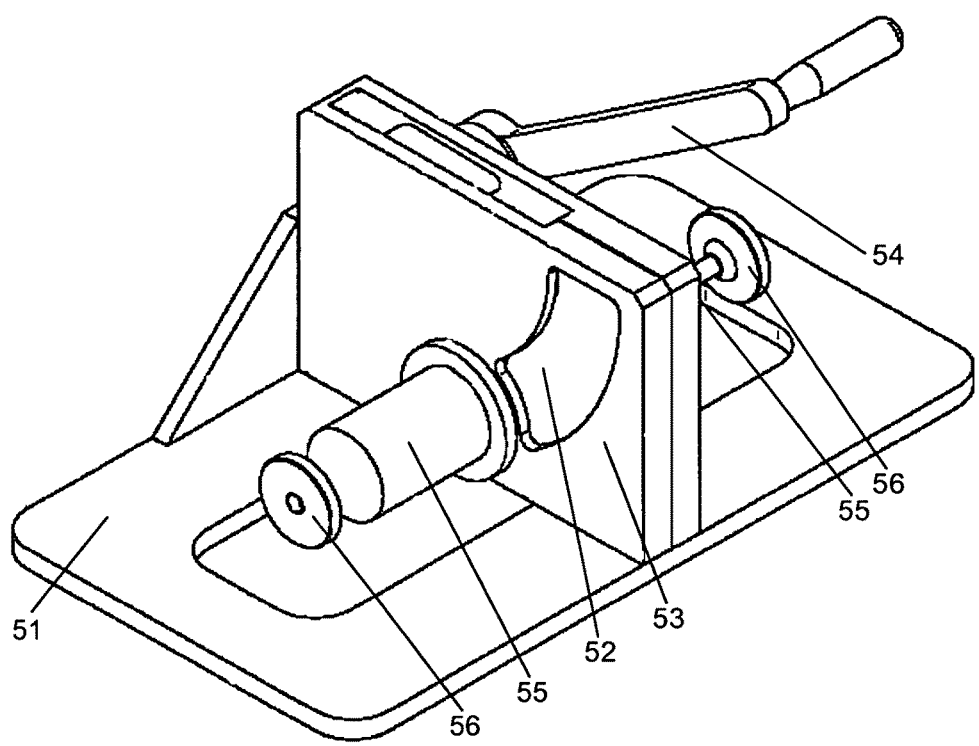
FIG. 11 is a perspective view of the macrotome tool.

The macrotome tool is illustrated in FIG. 11 and consists of a base plate 51, cutting blade 52, cutting blade enclosure 53, cutting blade handle 54, and two tissue specimen holders 55 equipped with moveable plungers 56.

Figure 12A:
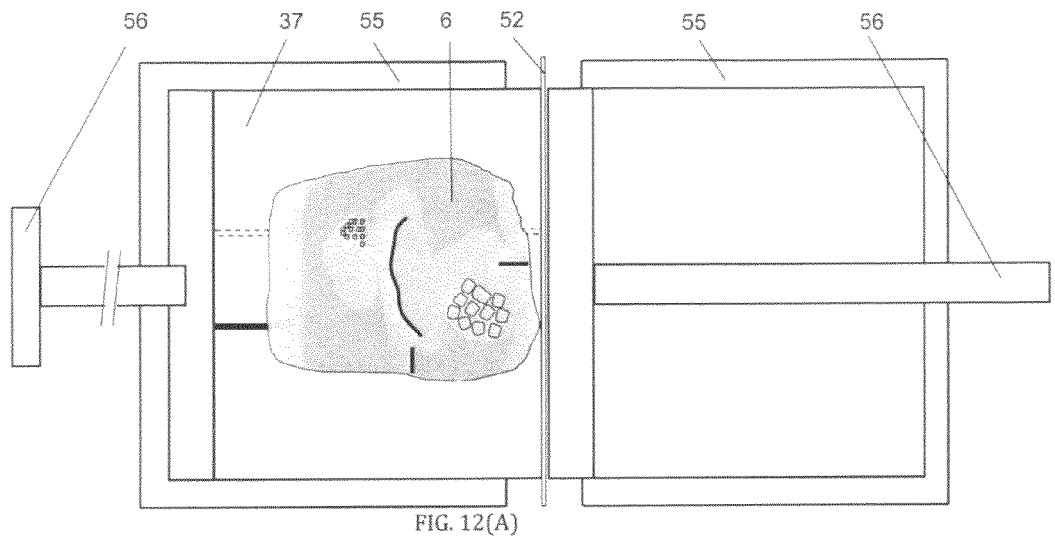
FIG. 12(A) shows the tissue specimen in the paraffin mold prior to cutting.

As illustrated in FIG. 12(A), the paraffin mold 37 is positioned in the tissue specimen holder 55 such that when the tissue specimen holder 55 is attached to the cutting blade enclosure 53, the tissue specimen 6 is directly abutting the macrotome cutting blade 52. In addition, when the tissue specimen holder 55 is attached, the needle track 41 and 42 are perpendicularly aligned with the macrotome cutting blade 52.

Figure 12B:
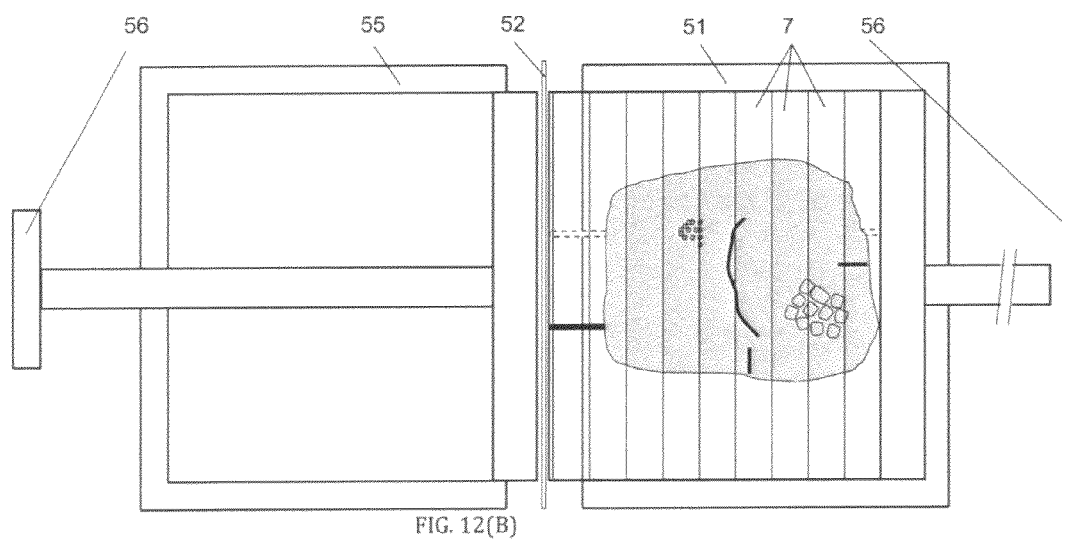
FIG. 12(B) shows the tissue specimen after cutting with the tissue specimen cut into tissue specimen blocks of equal thickness.

Once the tissue specimen holder 55 is attached, another empty tissue specimen holder 55 is positioned at the opposite side of the cutting blade 52 (see FIG. 12(A)). The cutting blade 52 is released using the cutting blade handle 54 and the tissue specimen embedded within the paraffin molds is advanced incrementally at pre-defined length intervals using the moveable plunger 56. The increment depends on the application and size of the tissue specimen. For cervical tissue samples, an increment of 0.5 mm is preferred. When the desired thickness (which again depends on the application and size of the tissue specimen but which in the presently preferred embodiment is either 2.5 mm or 3.0 mm), is achieved, the macrotome cutting blade 52 is advanced through the tissue specimen using the blade handle 54. This process is repeated until the entire length of the tissue specimen is traversed, and precisely cut tissue specimen blocks 7 perpendicular to the needle track are generated and collected by the opposite place tissue specimen holder 55 (see FIG. 12(B)). The paraffin block is taken out of the specimen holder 55 and the paraffin is broken away from the tissue specimen blocks while maintaining the sequence of blocks perpendicular to the needle tracks. The tissue specimen blocks are then placed in standard tissue cassettes preferably with the firstly cut block labeled A, the second block B, and so on.

Figure 13A:
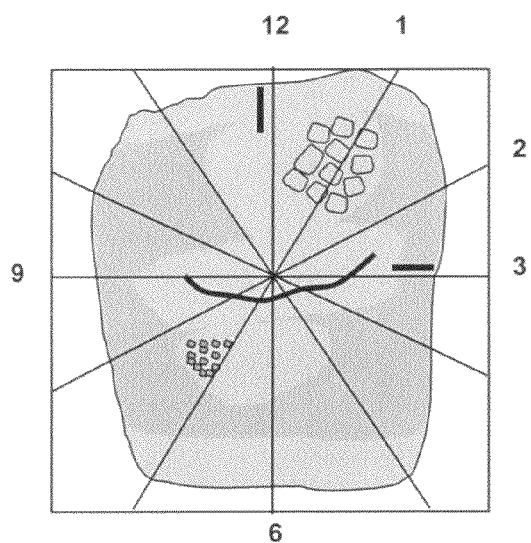
FIG. 13(A) shows the radial cutting.
Figure 13B:
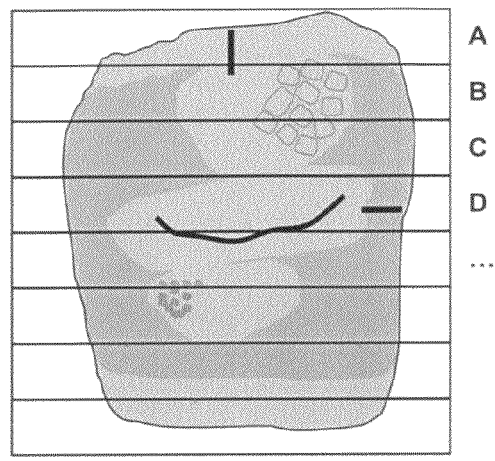
FIG. 13(B) shows the parallel cutting employed in the preferred embodiment of the present invention.

The tissue block cutting procedure of the macrotome tool differs from the standard procedure used in most hospitals worldwide to evaluate a tissue specimen of a cone biopsy from the cervix, independent of whether the cone was performed with a LEEP procedure or a cold knife/laser conization procedure (S. Palsson, U. Stenram, M. Soto Thompson, A. Vaitkuviene, V. Poskiene, R. Ziobakiene, J. Oyama, M. J. DeWeert, U. Gustafsson, N. Bendsoe, S. Andersson-Engels, S. Svanberg, and K. Svanberg, "Methods for detailed histopathological investigation and localization of biopsies from cervix uteri to improve the interpretation of autofluorescence data", Journal of Environmental Pathology, Toxicology, and Oncology 25, pp. 321-340, 2006, and S. Y. Park, M. Follen, A. Milbourne, H. Rhodes, A. Malpica, N. Mackinnon, C. MacAulay, M. K. Markey, and R. Richards-Kortum, "Automated image analysis of digital colposcopy for the detection of cervical neoplasia", J. Biomed. Opt. 13, pp. 014029-1-10, 2008, both incorporated herein by reference). In the standard procedure, the tissue specimen is first cut and then stretched out and pinned down to a special paper and placed in formalin. The specimen is then further cut in 12 pieces representing twelve radial sections as schematically illustrated in FIG. 13(A). The histopathology analysis presents its findings with reference to this circular coordinates system. This system typically gives more information on the central parts where the probability of cervical lesions is higher than on the outer parts. This method works fine when the pathological diagnosis goes back to the physician who is most interested to know the severity of the lesion and where the lesion is radially cut. However, this method makes it difficult to track what pathological section corresponds to what region in the digital image of the cervix. In the presently preferred embodiment, an x-y coordinate system is used to keep track of the spatial coordinates between the pathological sections and the colposcopic image. By cutting the specimen in parallel sections, sometime referred to as "bread-loafing" cutting and illustrated in FIG. 13(B), it is easier to visualize the specimen and the lesion in both two and three dimensions.

3. Histopathology Processing

Figures 14A, 14B, 14C, 14D:
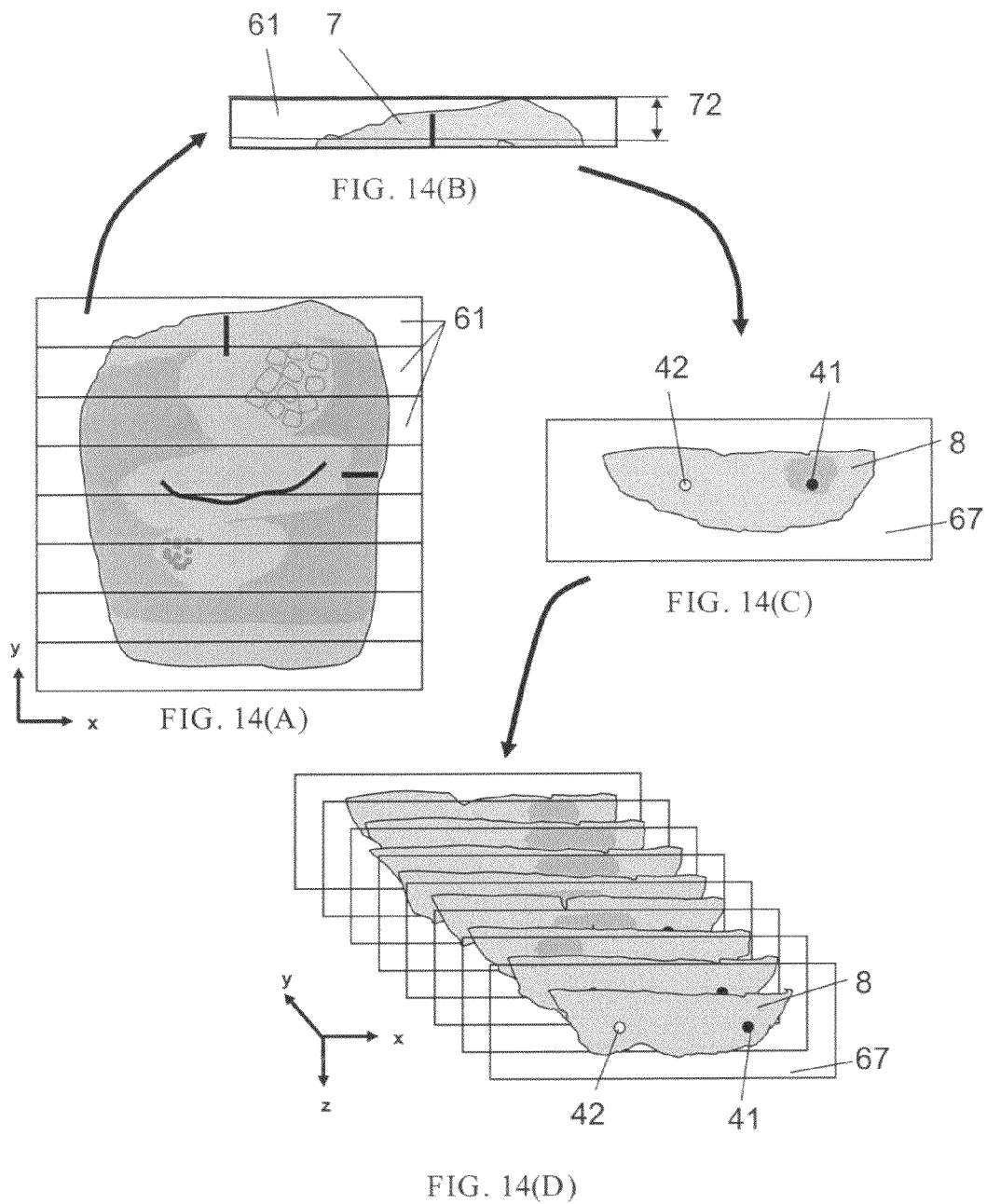
FIG. 14(A) shows the tissue specimen cut into tissue specimen blocks.
FIG. 14(B) shows how a tissue specimen block is sliced using the microtome until the tissue specimen slice is representative of the width of the tissue specimen.
FIG. 14(C) shows a tissue specimen slice placed on a microscope slide.
FIG. 14(D) shows the tissue specimen slices on the microscope slides after microtome cutting.
Figure 15:
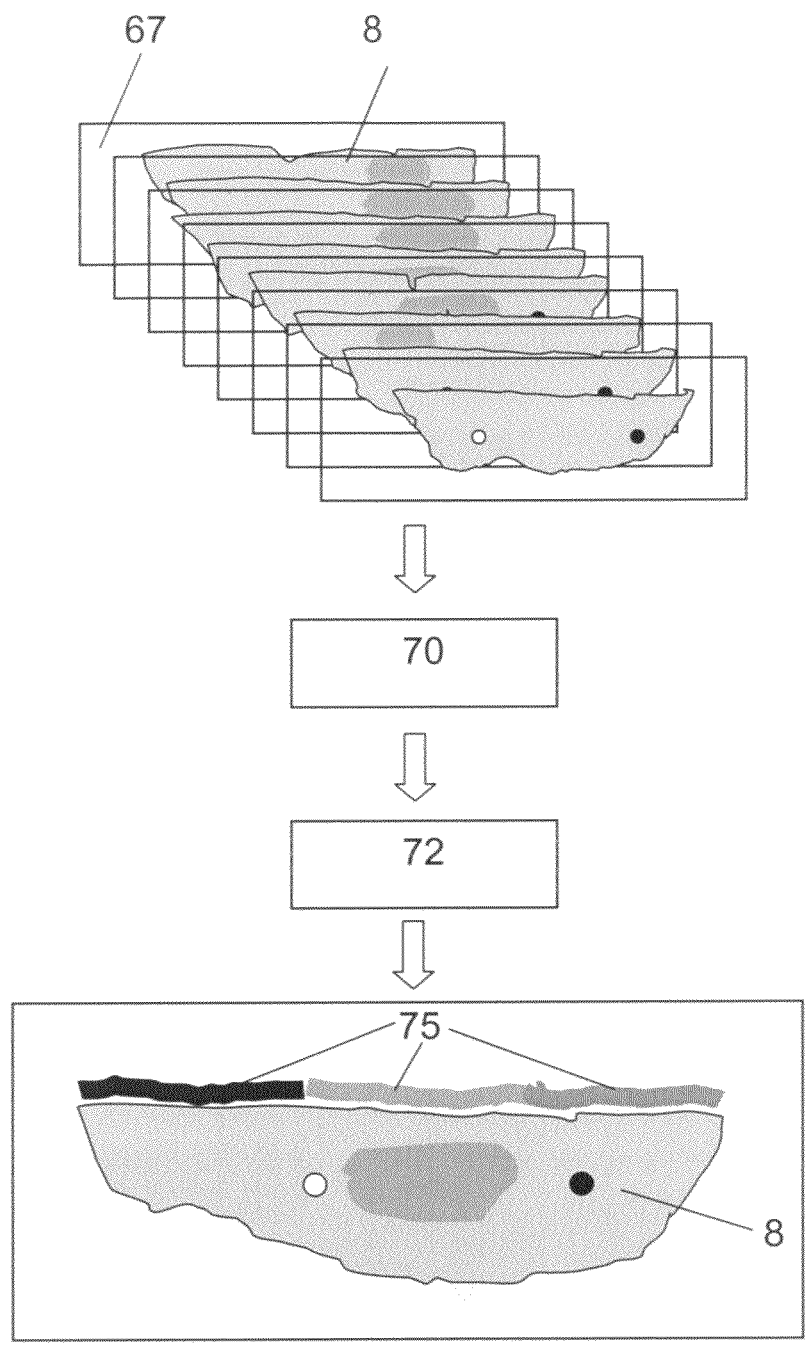
FIG. 15 is a flow chart of the histopathology annotation procedure.

After tissue sectioning with the macrotome tool, a number of tissue specimen blocks 7 have been generated and placed in standard tissue cassettes 61, as schematically illustrated in FIG. 14(A). The first cassette is then placed in a standard microtome cutter for further sectioning of the tissue specimen block. A microtome is a mechanical instrument used to cut the tissue specimen blocks into transparent thin sections for microscopic examination with a thickness varying from about 2 to 25 micrometer. The tissue specimen blocks are sliced using the microtome until the specimen slice is representative of the width of the tissue specimen (see FIG. 14(B)). The amount of tissue discarded 65 are measured and recorded. A tissue specimen slice 8 is then sectioned off and placed on a microscope slide 67 (see FIG. 14(C)). This process is repeated for all the remaining tissue cassettes, and a set of microscope slides 67 with tissue specimen slices 8 are available for detailed pathology analysis (see FIG. 14(D)). As illustrated in FIG. 15, the combined processing and cutting procedure of the needle guide, macrotome, and microtome results in tissue specimen slices 8 with ink dots 41 and 42 as reference points in each tissue specimen slice 8.

After microtome sectioning, the tissue microscope slides 67 with the tissue specimen slices 8 are digitized using a pathology image scanning system 70 (see FIG. 15). These digitized tissue slides are then reviewed and histopathology annotated 72 according to standard pathology procedures or in support of the development of computer aided detection systems. In the application of detecting cervical cancer and the presently preferred embodiment, preferably eighteen epithelial findings are identified: 1) Surface epithelium, 2) Needle injection sites, 3) Basement membrane, 4) Destroyed surface epithelium, 5) No epithelium, 6) Normal squamous epithelium, 7) Normal glands, 8) Immature squamous metaplasia, 9) Reactive glandular epithelium, 10) Marked (severe) inflammation, including follicular cervicitis, 11) Atypical immature metaplasia, 12) Over gland extension, 13) Low grade squamous intraepithelial lesion (LSIL), 14) High grade squamous intraepithelial lesion (HSIL)—Cervical intraepithelial neoplasia 2 (CIN 2), 15) High grade squamous intraepithelial lesion (HSIL)—Cervical intraepithelial neoplasia 2-3 (CIN 2-3), 16) High grade squamous intraepithelial lesion (HSIL)—Cervical intraepithelial neoplasia (CIN 3), 17) Squamous cell carcinoma, microinvasive <3 mm, and 18) Adenocarcinoma in situ.

In the preferred embodiment, each finding is uniquely coded, such as using different colors or a gray scale. FIG. 15 shows an example of a digitized tissue specimen slice 8 with gray scale coded pathology annotations 75.

Thus, unlike the conventional pathology report, which provides a single diagnostic outcome encompassing the "worst" of the lesion noted and representative diagnosis for future clinical management, the "linear" annotations of the current inventions provides diagnostic decision for every linear micron of the surface epithelium. Although the process is time-consuming, it provides enormous data enabling the assimilation of colposcopic assessment and underlying histopathology.

4. Histopathology Reconstruction

Figure 16:
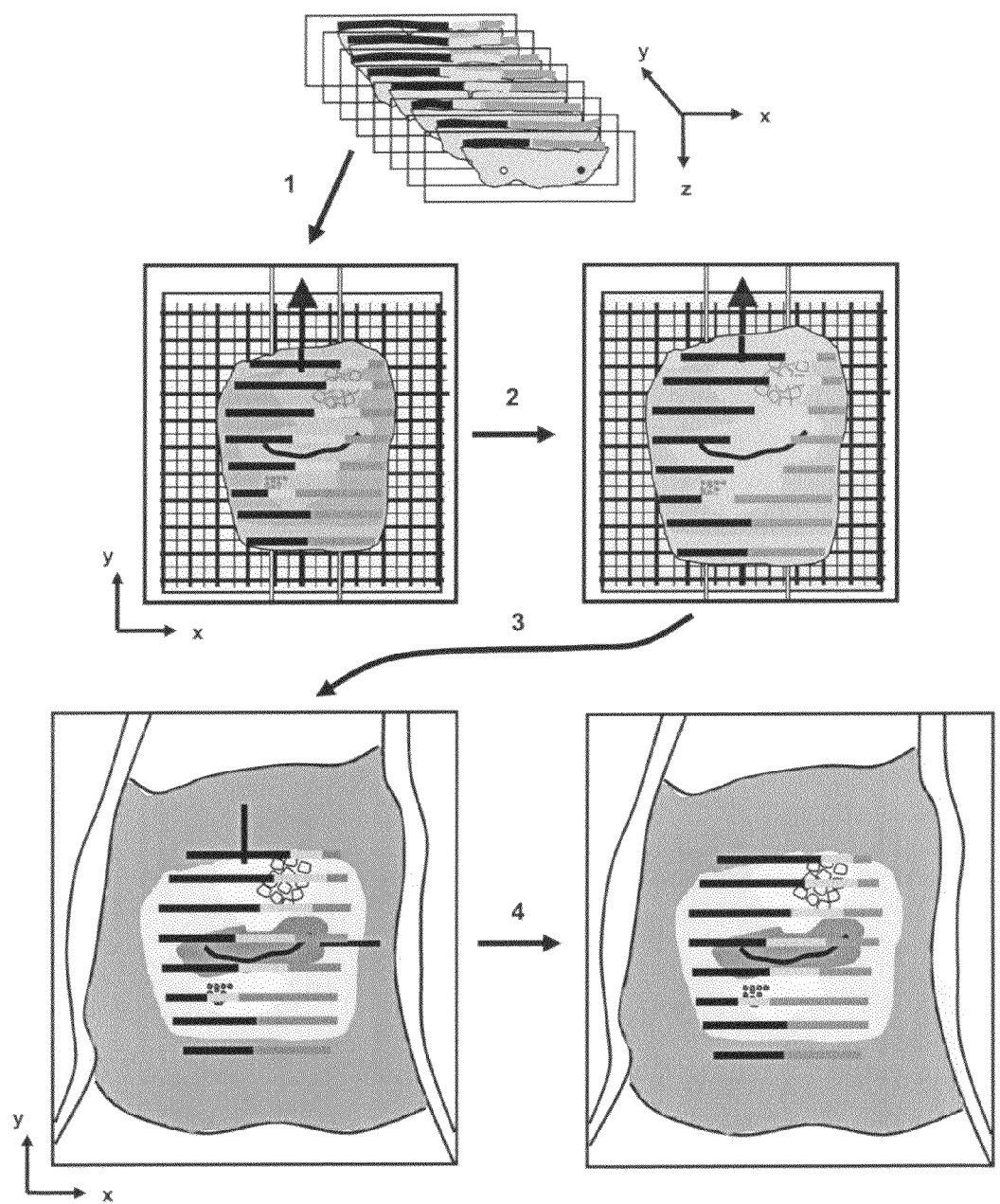
FIG. 16 is an illustration of the histopathology reconstruction process.

After the histopathology analysis, the final step of the current invention is to correlate the histopathology annotations back to the reference image of the area of investigation. This reconstruction, or mapping, procedure is schematically illustrated in FIG. 16 and consists of four main steps. The histopathology annotations are first back correlated to the fixed image (1). This is followed by three sequential image registration processes in which the fixed image is first registered to the specimen image (2), then the specimen image to the fiduciary image (3); and finally the fiduciary image to the reference image (4).

In step 1 the histopathology annotations are mapped to the fixed image according to the procedure illustrated in FIG. 17. First, the color of the left and right injection sites are located and determined. If the tissue slices have been flipped during the microtome histopathology process, the colors of the left and right injection sites have subsequently also been flipped. If this is the case, the tissue slide is flipped back to the correct orientation (see FIG. 17(A). The needle injection sites are then aligned horizontally and the histology annotations projected to the x-axis (see FIG. 17(B)).

Figure 17A:
FIG. 17(A) shows the alignment of the needle marks.
Figure 17B:
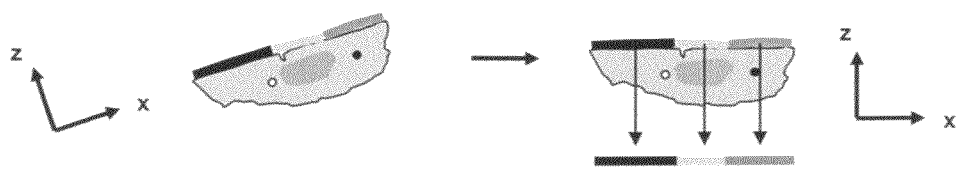
FIG. 17(B) shows the horizontal alignment of needle marks and the projection of the histology annotations to the x-axis.
Figure 17C:
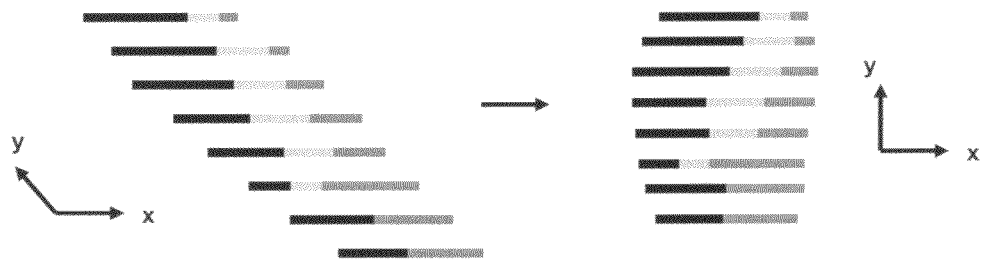
FIG. 17(C) shows the alignment of the histopathology annotations along the y-axis.

Using the locations of the tissue specimen blocks and slices as determined during the macrotome and microtome procedures, the histopathology annotations are then aligned along the y-axis of the fixed image (see FIG. 17(C)).

Figure 17D:
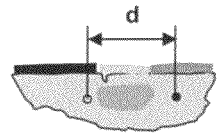
FIG. 17(D) shows the determination of the distances between the needle injection sites of the tissue specimen slice and the needle position in the fixed image.
Figure 17D:
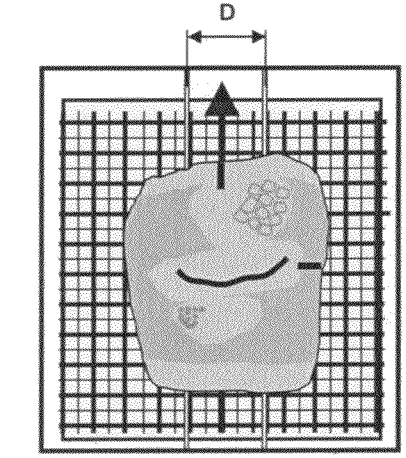

Any tissue shrinkage during the tissue and histopathology process is then determined (see FIG. 17(D)). First, the distance, d, between the needle injection sites on the horizontally aligned tissue slice annotations is measured. Next, the needles in the fixed image are located, and using the scale of the grid and alignment pattern the distance, D, between the needles in the fixed image is measured. Finally, the distances between the needle injection sites and the needle positions in the fixed image are compared and the tissue shrinkage, S, is calculated for each tissue slice, i, according to $$S_i = \frac{d_i}{D_i} \quad (1)$$

Following the calculation of the tissue shrinkage the tissue slice annotations are aligned on the fixed image and, if any shrinkage is present, stretched accordingly along the x- and y-axes (see FIG. 16).

In step 2 to 4 the fixed image and the corresponding histopathology annotations are registered to the reference image by applying three sequential image registration procedures (see FIG. 16).

The first image registration of the fixed image to the specimen image accounts for the shrinkage artifact caused by the formaldehyde fixation. The locations of the needles in the two images are used as landmarks for the image registration procedure.

The second image registration of the specimen image to the fiduciary image accounts for the image rotation caused by aligning the fiduciary marks to the grid and alignment pattern of the needle guide as well as tissue shrinkage and soft tissue movement caused by the tissue excision procedure. The fiduciary lines and geographical features of the area of investigation are used as landmarks for the image registration procedure.

The third and final image registration is that of the fiduciary image to the reference image and this step accounts for tissue translation and soft tissue movement between the image captures. The geographical features of the area of investigation are used as landmarks for the image registration procedure.

The image registration process of the present invention preferably includes robust and automated registration algorithms. With the use of mechanical landmarks (the needles), the first image registration preferably utilizes an affine transformation. However, any transformation that accounts for the tissue shrinkage can be used. For the second and third image registrations, an elastic image registration algorithm that accounts for soft tissue movement as well as translation and rotation is preferably used (as described in co-pending, commonly assigned U.S. patent application Ser. No. 12/221,645, entitled "Computerized Image Analysis for Acetic Acid Induced Cervical Intraepithelial Neoplasia", filed Aug. 26, 2008, incorporated herein as reference). However, any image registration that accounts for the soft tissue movement can be used.

Figure 2A:
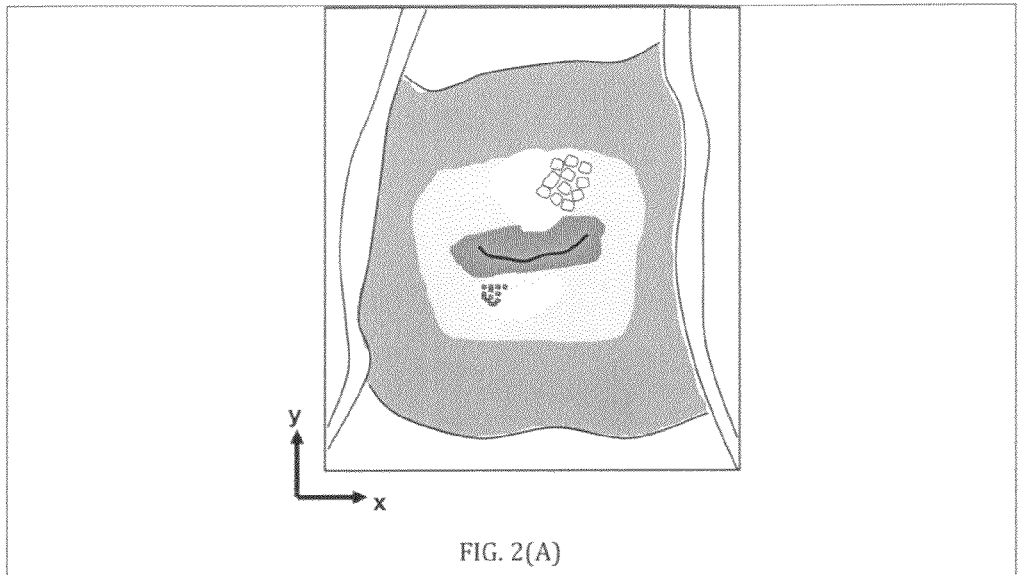
FIG. 2(A) shows an image of the cervix after the application of acetic acid; the reference image.
Figures 2B, 2C:
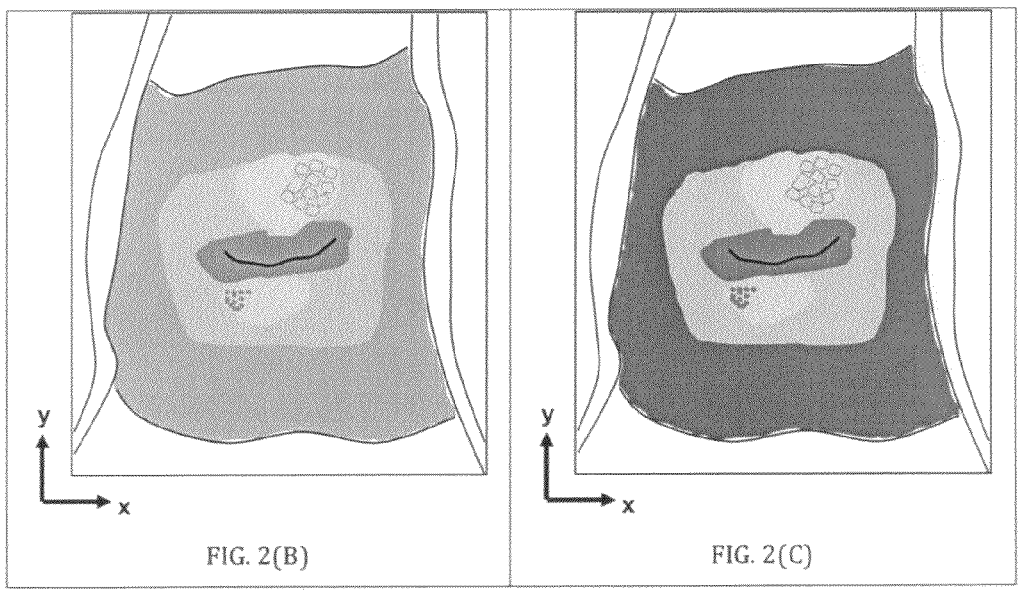
FIG. 2(B) shows an image of the cervix before the application of acetic acid.
FIG. 2(C) shows an image of the cervix after the application of Lugol's iodine. The surface of the cervix defines the two-dimensional, x-y, plane of the cervix.

Now the histopathology annotations are accurately mapped back to the reference image. This reconstructed histopathology map provides the gold standard for colposcopy assessment and computer aided detection systems. If additional images are acquired during the clinical procedure, such as the pre-acetic acid image and the Lugoul's iodine image in colposcopy (see FIG. 2), additional image registration can be applied to map the histopathology annotations from the reference image to these additional images. As soft tissue movement is likely between the image capture of these image, an elastic registration algorithm are preferably employed (as described in co-pending, commonly assigned U.S. patent application Ser. No. 12/221,645, entitled "Computerized Image Analysis for Acetic Acid Induced Cervical Intraepithelial Neoplasia", filed Aug. 26, 2008, incorporated herein as reference).

INDUSTRIAL APPLICABILITY

This invention is applicable whenever it is desirable to maintain 3 dimensional orientation between a specimen, and images from slices of the specimen, so as to register annotations of analyses of various locations on the specimen with an image of the specimen. More broadly, this invention is applicable whenever it is desired to maintain 3 dimensional orientation of a specimen that is sliced for analysis (tomographic analysis) with respect to the object or environment from which the specimen was taken, which is not necessarily limited to medicine. For example, it may be important to preserve orientation information about geological samples that are sliced for analysis, to preserve information about orientation of magnetic materials embedded in the samples with respect to the Earth's magnetic field at the location where the sample was taken. For a further example, it may be important to preserve orientation information about structural materials that have failed and are sliced for analysis, to preserve information about the direction of stresses that may have been applied. Thus, this invention is applicable whenever orientation of an excised specimen must be preserved, while a tomographic analysis is performed. Accordingly, no limitations are to be implied in the scope of the invention, except as specifically and explicitly stated in the claims.

What is claimed is:

1. A process for maintaining 3 dimensional orientation between a tissue specimen excised from an area of investigation on a body during clinical examination, and images of the surface of said area of investigation prior to removing said tissue specimen, to register histopathologic diagnoses of multiple locations within said specimen back to corresponding locations on the surface of said area of investigation on said body, comprising:

acquiring a reference image of said surface of said area of investigation on said body prior to removing said tissue specimen;

marking at least two fiduciary lines on tissue of said area of investigation on said body at appropriate positions as not to obscure or destroy diagnostically significant information;

acquiring a fiduciary image of the surface of said tissue on said body with said fiduciary lines prior to removing said tissue specimen;

excising said tissue to form said tissue specimen;

inserting at least two parallel needles through said specimen;

acquiring a specimen image of said specimen and said inserted needles over an alignment grid;

fixing said specimen, whereby a fixed specimen is formed;

acquiring a fixed image of said fixed specimen and said inserted needles over said alignment grid;

forming a paraffin mold containing said fixed specimen and said inserted needles;

injecting different colored inks through said needles while withdrawing said needles from said fixed specimen, whereby different colored needle tracks are formed in said specimen;

sectioning said specimen to create specimen blocks having said different colored needle tracks;

further sectioning said specimen to cut said specimen blocks into specimen slices having different colored ink dots corresponding to said different colored needle tracks, whereby said different colored ink dots serve as reference points;

forming pathology images from said specimen slices;

performing histopathology analyses on said pathology images;

annotating said pathology images with histopathology annotations;

aligning said annotations with said fixed image using said reference points;

determining shrinkage between said fixed image and said annotations by comparing the distance between said needles on said grid in said fixed image with the distance between said reference points on said specimen slices in said pathology images;

registering said fixed image to said specimen image to account for shrinkage caused by fixation, by using locations of said needles in both of said images as landmarks; and registering said specimen image to said fiduciary image to account for tissue translation and soft tissue movement of said specimen between said specimen image and said

19 fiduciary image using a first image registration algorithm that accounts for soft tissue movement, and said alignment grid;

registering said fiduciary image to said reference image to account for tissue translation and soft tissue movement of said tissue between said fiduciary image and said reference image using said fiduciary lines and geographical features of said area of investigation as landmarks and said first image registration algorithm or a second image registration algorithm that accounts for soft tissue movement;

whereby annotations of histopathologic diagnoses are provided for multiple locations on or under the surface of said specimen that are shown in said fiduciary image of said specimen.

2. A process according to claim 1, wherein said inserting step is performed using at least three parallel needles, whereby any bending of said specimen can be detected.

3. A process according to claim 1, wherein said fixing step is performed by immersing said specimen and said inserted needles in a fixing material selected from the group consisting of formaldehyde, glutaraldehyde, tannic acid, picric acid, absolute alcohol, potassium dichromate, mercuric chloride and osmium tetroxide.

4. A process according to claim 1, wherein said fixing step is performed using a process selected from the group consisting of rapid heating and quick-freezing of said specimen and said inserted needles.

5. A process for registering histopathologic diagnoses of multiple locations within a tissue specimen from an area of investigation on a body during clinical examination back to corresponding locations on the surface of said area of investigation on said body prior to removing said tissue specimen, comprising:

maintaining three dimensional orientation between said specimen and said surface of said area under investigation on said body prior to removing said tissue specimen by:

marking fiduciary lines on tissue of said area of investigation on said body prior to removing said tissue specimen;

acquiring a fiduciary image of said area of investigation on said body and said fiduciary lines prior to removing said tissue specimen;

excising said tissue to form said tissue specimen;

inserting at least two parallel needles through said specimen;

acquiring a specimen image of said specimen and said inserted needles over an alignment grid;

forming at least one colored needle track in said specimen using at least one of said needles;

sectioning said specimen into specimen slices having at least one colored ink dot corresponding to said at least one colored needle track, whereby said at least one colored ink dot and an uncolored dot formed by any uncolored needle track serve as reference points;

performing histopathology analyses on said specimen slices;

annotating pathology images of said specimen slices with histopathology annotations;

registering said annotations with said specimen image using said reference points;

determining shrinkage between said specimen image and said annotations by comparing the distance between said needles on said grid in said specimen image with the distance between said reference points; and

20 registering said specimen image to said fiduciary image using an image registration algorithm that accounts for soft tissue movement and said grid;

whereby annotations of histopathologic diagnoses are provided for multiple locations on or under the surface of said area of investigation that are shown in said fiduciary image.

6. A process for maintaining three dimensional orientation between a tissue specimen from an area of investigation on a body during clinical examination with corresponding locations on the surface of said area of investigation prior to removing said tissue specimen, comprising:

marking fiduciary lines on tissue of said area of investigation on said body prior to removing said tissue specimen;

acquiring a fiduciary image of said area of investigation on said body and said fiduciary lines prior to removing said tissue specimen;

excising said tissue to form said tissue specimen;

forming at least two parallel needle tracks in said specimen by inserting at least two parallel needles through said specimen;

coloring at least one of said needle tracks to form at least one colored needle track;

acquiring a specimen image of said specimen and said inserted needles over an alignment grid; and sectioning said specimen into specimen slices having at least one colored ink dot corresponding to said at least one colored needle track, whereby said at least one colored ink dot and an uncolored dot formed by any uncolored needle track serve as reference points;

whereby images of said specimen slices can be registered to said specimen image using said reference points; and whereby said specimen image can be registered to said fiduciary image using registration algorithm that accounts for soft tissue movement and said alignment grid.

7. A process for maintaining three dimensional orientation between a material specimen from an area of investigation on a body during clinical examination with corresponding locations on the surface of said area of investigation prior to removing said tissue specimen, comprising:

marking fiduciary lines on material of said area of investigation on said body prior to removing said tissue specimen;

acquiring a fiduciary image of said area of investigation on said body and said fiduciary lines prior to removing said tissue specimen;

excising said material to form said material specimen;

forming at least two tracks through said specimen;

coloring at least one of said tracks to form at least one colored track;

acquiring a specimen image of said specimen and said tracks over an alignment grid; and sectioning said specimen into specimen slices having at least one colored ink dot corresponding to said at least one colored track, whereby said at least one colored ink dot and an uncolored dot formed by any uncolored track serve as reference points;

whereby images of said specimen slices can be registered to said specimen image using said reference points; and whereby said specimen image can be registered to said fiduciary image using an image registration algorithm that accounts for soft tissue movement and said alignment grid.

* * * * *